United States Patent [19]

Heisinger, Jr.

[11] Patent Number: 5,735,864
[45] Date of Patent: Apr. 7, 1998

[54] DISPOSABLE TONGUE CLEANER

[76] Inventor: Charles G. Heisinger, Jr., 1032 Hull Ter., Evanston, Ill. 60202

[21] Appl. No.: 808,109

[22] Filed: Feb. 28, 1997

[51] Int. Cl.$^6$ ................................................ A61B 17/24
[52] U.S. Cl. ................................................ 606/161; 15/111
[58] Field of Search .............................. 606/161, 159, 606/235; 15/110, 111, 114

[56] References Cited

U.S. PATENT DOCUMENTS

| | | | |
|---|---|---|---|
| 1,891,864 | 12/1932 | Barrett | 606/161 |
| 2,218,072 | 10/1940 | Runnels | 606/161 |
| 5,226,197 | 7/1993 | Nack et al. | 606/161 |

Primary Examiner—Michael Buiz
Assistant Examiner—Kevin Truong

[57] ABSTRACT

A disposable oral-hygiene instrument for loosening, collecting, and removing debris from the surface of the tongue. The device comprises a handle at one end with a textured surface at the other end for scrubbing the dorsal surface of the tongue. Along the distal perimeter edge of the scrubbing surface extends a scraper for moving debris from the back to the front of the tongue. Affixed to the same end of the instrument as the scrubbing surface is an absorbent material for collecting and removing debris. The instrument is designed to avoid gag reflex due to its low profile.

15 Claims, 2 Drawing Sheets

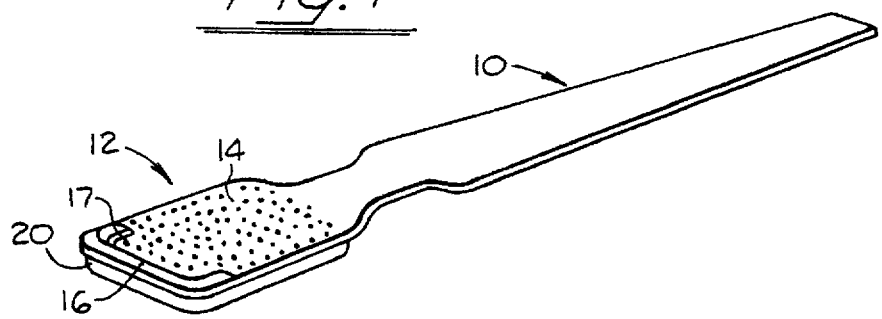
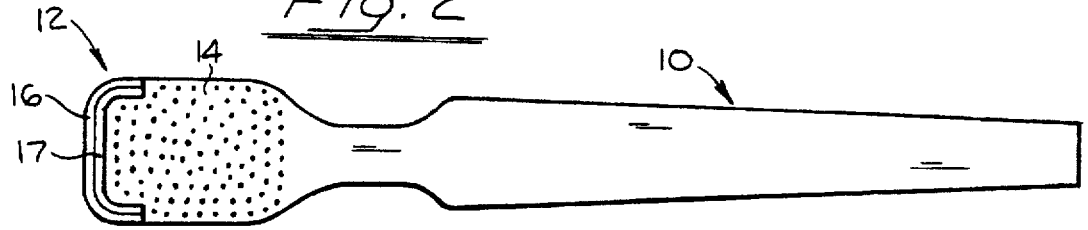
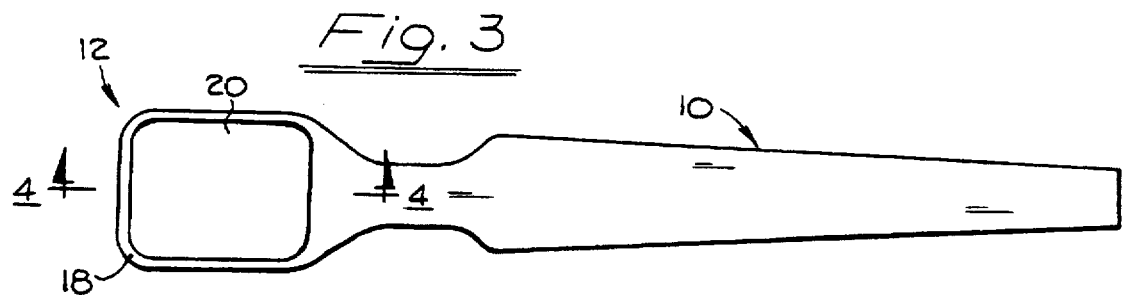
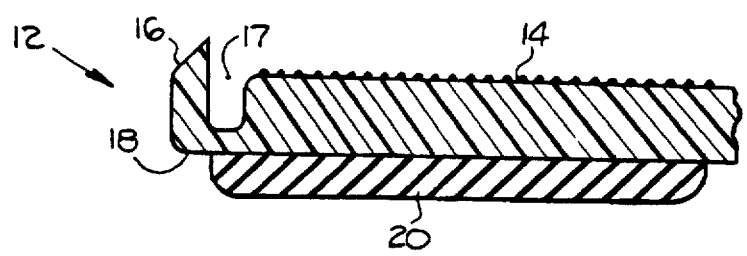

DISPOSABLE TONGUE CLEANER

BACKGROUND

1. Field of the Invention

This invention relates to a disposable oral hygiene device comprising a handle, an abrasive, textured surface, an absorbent material and a flavored medicament for the purpose of removing foreign matter from the dorsal, or top, surface of the tongue.

2. Prior Art

At the present time, the applicant is unaware of any existing prior art devices which are in common usage and which would enable the dorsal surface of the tongue to be properly cleaned in a convenient manner.

To date, tongue cleaners have consisted of conventional toothbrushes applied to the tongue, and different kinds of tongue scrapers. The applicant is unaware of any device which combines the benefits of ease of use, convenience, portability, and disposability.

The dorsal surface of the tongue is covered with papillae. The anterior two-thirds of the dorsal surface is covered with short fungiform papillae while the posterior third is covered with 2 to 3 mm. long filiform papillae. Bacteria, food particles, the breakdown products of food, and putrefied post-nasal drip are trapped in the crevices between the papillae, particularly on the posterior third of the dorsal surface of the tongue. The posterior area of the dorsal surface of the tongue is the most frequently overlooked source of oral malodor. [Rosenberg, JADA, 127:481 (1996)]

A number of devices purporting to clean the tongue have been advanced over the last 3 decades. U.S. Pat. No. 3,943,592 discloses a tongue depressor with a securing tape of "Velcro" attached to it. While this device appears to loosen some debris on the posterior third of the tongue, the tape, which is comprised of small "hooks", is not very absorbent and does not appear to actually collect or remove substantial amounts of debris from the mouth.

U.S. Pat. No. 4,079,478 embodies a tongue brush mounted on a support frame. This device is not convenient for use, given its lack of portability due to its awkward shape, which includes a "pistol" grip, and requires cleaning after each use.

U.S. Pat. No. 5,226,197 shows a tongue hygiene device that combines short brushes and a scraper. This device is of questionable cost to mass produce for disposable use, does not appear to absorb significant quantities of debris given the short brushes on the device, and accordingly would require a water source to continually rinse the device during brushing, thereby diminishing ease of use.

U.S. Pat. No. 5,282,814 comprises a scraper with an antiseptic pad. In both embodiments presented, the blade, due to its height, appears to be capable of eliciting gag reflex, a reaction caused by touching the pharynx or soft palate. Additionally, this device in not disposable and requires cleaning and storage after each use.

OBJECTS AND ADVANTAGES

It is an object of the present invention to provide a disposable tongue cleaner which can loosen and remove food, debris, plaque, post-nasal drip from the folds and papillae on the dorsal surface of the tongue.

It is a further object to provide a device capable of thoroughly attracting and accumulating the loosened debris, so as to assuredly contain, transport, and thereby expel it from the oral cavity.

It is a further object to provide a portable device, which may be easily transported and does not require a water source for rinsing the instrument during or after cleaning.

It is a further object of the invention to provide a disposable device, which can be constructed simply and at such cost to permit disposal and repurchase of the product on a frequent basis. Disposability is desirable from a hygienic and aesthetic viewpoint.

It is a further object to provide an embodiment which can be coated with an antiseptic medicament and a flavoring agent to enhance cleansing and deodorizing action of the device.

It is a final object of the invention to provide a device which, because of its design, does not elicit gag reflex.

BRIEF DESCRIPTION OF THE DRAWINGS

FIG. 1 is a perspective view of the device of the invention.

FIG. 2 is a top view showing the textured surface, and scraper.

FIG. 3 is a bottom view with the absorbent surface.

FIG. 4 is a sectional view of the device.

DETAILED DESCRIPTION OF THE DRAWINGS

Figure 5:
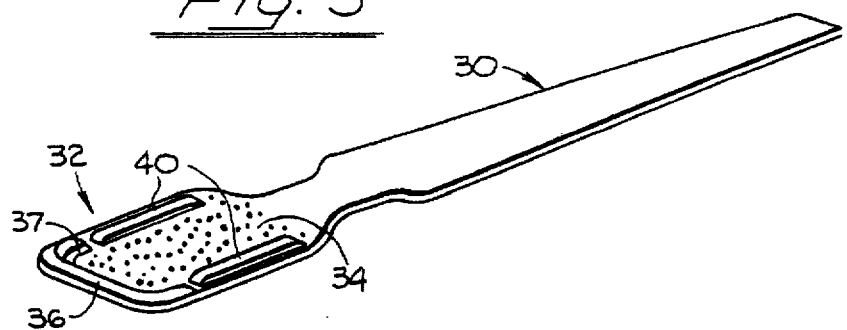
FIG. 5 is a perspective view of a second embodiment of the invention.

The preferred embodiment of the tongue cleaner is illustrated primarily in FIG. 1. The cleaner is comprised of an elongated body or member with handle 10 attached to or integral with an enlarged head 12. The top side of the enlarged head 12 features a shaped, textured surface 14.

Referring to FIG. 2, the enlarged head 12 has, extending along the perimeter of its distal end, a scraper 16. Adjacent to the interior side of the scraper 16 is a transverse trough 17.

FIG. 3 illustrates the bottom surface 18 of the head, affixed to which is an absorbent material 20, preferably extending throughout the surface.

FIG. 4 depicts the detail of elements existing on enlarged head 12. The absorbent material 20, as seen in FIG. 3 and FIG. 4, made of polyurethane or other absorbent material, adheres to the surface 18 by application of adhesive to the surface.

Figure 6:
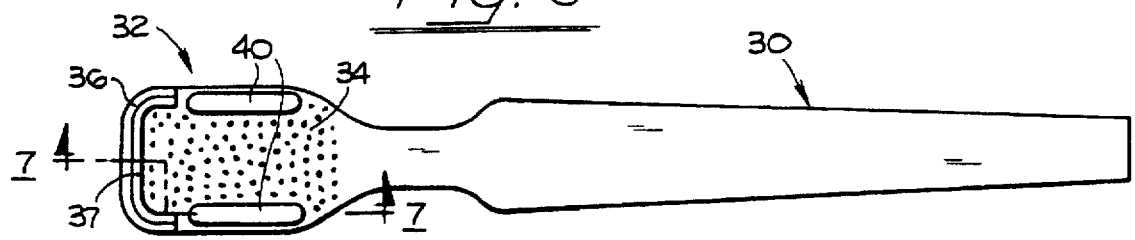
FIG. 6 is a top view of FIG. 5.
Figure 7:
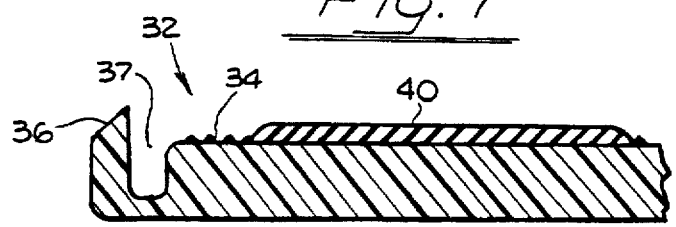
FIG. 7 is a sectional view of FIG. 5.

FIGS. 5, 6, and 7 show a second embodiment of the invention. In this embodiment, an enlarged head 32 is at the distal end of a handle 30, where two strips of absorbent material 40 are affixed on the same side, i.e. the top side, of the head as is a texture surface 34. In this embodiment, a scraper 36 extends along a portion of the perimeter of the enlarged head 32. A transverse trough 37 extends along the interior side of the scraper 36 and partially along the sides of the textured surface 34.

In both embodiments presented, the handle is preferably of a flexible plastic, such as polyethylene. The handle, however, if desired, be made of any other materials that can be bent slightly without fracturing, such as polypropylene, vinyl, nylon, rubber, various plasticised materials, cardboard, etc.

In the foregoing embodiments, the textured surface, 14 or 34, is an integral part of the handle. However, a textured material may be manufactured separately and adhered by application of an adhesive to the desired area on the enlarged head.

Figure 8:
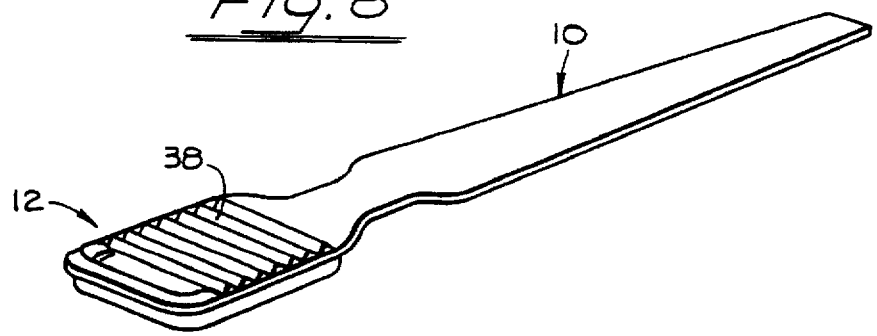
FIG. 8 is a perspective view of a third embodiment of the invention, featuring a saw-tooth textured surface.

In the above structures, the textured surface has an abrasive, sandpaper-like appearance, but it can instead be made of any other shape or pattern which effectively gathers debris, such as a ribbed-shape, or sawtooth-groove pattern, as shown at 38 in FIG. 8, extending from the desired area on the enlarged head.

In the above devices, the absorbent material consists of polyurethane, but if desired it can be made of any other material or combination of materials which collect and retain debris, such as sponge, paper, cardboard, cloth, cotton, or other materials.

In the embodiments presented, the scraper is an integral part of the handle enlarged head.

In any of the devices, a medicament consisting of an antiseptic and a flavoring agent is applied at the time of manufacture to the head of the cleaner.

Operation of the Device

In operation, the tongue cleaner is grasped in either hand by the handle 10. The enlarged head 12 of the cleaner is inserted into the mouth with the scraper 16 and textured surface 14 facing down, towards the dorsal surface of the tongue. The head is placed on the posterior one-third of the tongue and repeatedly pulled forward towards the anterior portion of the tongue. The textured surface 14 makes contact with the dorsal surface of the tongue and scrubs and loosens debris from the folds between papillae. As the debris is loosened, it is moved towards the anterior part of the tongue by the scraper 16. When the loosening of debris is completed, the cleaner is turned over so that the side with the absorbent material 20 faces downward towards the dorsal side of the tongue. A side-to-side movement of the head across the tongue collects the debris in the absorbent material. The debris is thus removed by the cleaner from the surface of the tongue and the oral cavity.

In the second embodiment presented, the cleaner is not rotated because the absorbent material 40 appears in two places on the same side of the enlarged head 32 as the textured surface 34 and scraper 36.

In both embodiments, a coating comprised of antiseptic and flavoring on the enlarged head is transferred to the surface of the tongue during operation. The coating kills bacteria and produces a pleasant flavor.

Conclusions, Ramifications, and Scope

Accordingly, it will be seen that this tongue cleaner easily loosens, collects and removes debris from the dorsal surface of the tongue. None of the above patents show devices that actually contain and expel the debris all together by the action of scraping the tongue, by means of the absorbent material. Additionally, the device is portable and disposable, permitting single-use functionality. The single-use function permits a medicament to be applied to the tongue, so as to improve cleansing and provide a pleasant taste after use. Furthermore, a number of other consequences and advantages derive from this cleaner in the following areas:

Ease of Manufacture. The tongue cleaner is comprised of relatively few elements. In the embodiments where the textured surface is molded on the body and the absorbent material is adhered to the body, there are only three manufactured elements: the body, the absorbent material, and the applied medicament. This simple design results in a low cost of manufacture.

Single-Use Function. A direct consequence of this tongue cleaner's low manufactured cost is its single-use design. The single-use function provides the user with a new cleaner for each use. Packaging serves to ensure the cleanliness of each cleaner prior to use. The single-use design alleviates the need for between-use storage, which is required with a multi-use instrument. It would not be feasible to pre-apply medicament at the time of manufacture to a device made for repeated use. The other benefit from single-use design is disposability. Disposability is highly desirable from a sanitary and convenience perspective. Collected debris may be immediately discarded in a sanitary manner, rather than merely rinsed off after each use. Often stains and mucous debris cannot be rinsed off, making the instrument unsightly and unsanitary.

Removal of Debris. The tongue cleaner disclosed here functions to collect and remove debris from the oral cavity. Many scrapers only relocate tongue debris from the posterior to the anterior area of the tongue. Debris may recollect in the posterior area if an attempt is made to swallow it.

Although the description above contains many specificities, these should not be construed as limiting the scope of the invention but as merely providing illustrations of some of the presently preferred embodiments of the invention.

Thus the scope of the invention should be determined by the appended claims and their legal equivalents and not only by the examples given.

I claim:

1. An oral-hygiene device for cleaning the tongue comprising:

a. a one piece elongated body having a proximate end for grasping in either hand and a distal end having two substantially flat surfaces on respectively opposite sides, a first and a second surface, b. said distal end having a perimeter edge, c. said first surface being formed and shaped into a textured surface for scrubbing and loosening debris located on the surface of the tongue, and d. located on said second surface is means forming a collecting means for collecting and removing said debris from the mouth, whereby said device, in response to movement thereof over the tongue, collects, and removes debris from the top surface of the tongue.

2. The device of claim 1 wherein, the collecting means is an absorbent material.

3. The device of claim 2 wherein, the absorbent material is in the form of a single continuous element secured to said second surface.

4. The device of claim 2 wherein, the absorbent material includes a pair of strips spaced apart and positioned on said first surface at the side edges thereof.

5. The device of claim 1 wherein, said body is composed of polyethylene.

6. The device of claim 1 wherein, said body is composed of wood.

7. The device of claim 1, further including, a scraper on said distal end and extending along said perimeter thereof.

8. The device of claim 7, further including, said trough having an interior side extending along said interior side of said scraper and adjacent thereto.

9. The device of claim 1, further including, the application of an antibacterial medicament to said distal end of said body.

10. The device of claim 1 wherein, the elements forming the texture of the textured surface are integral with the body.

11. A device for cleaning the tongue, comprising:
 a. an elongated, planar member having a perimeter edge and having a distal end and a textured surface at said distal end for loosening particles from the surface of the tongue,
 b. an absorbent surface located on said distal end of said member for collecting and removing said debris from mouth
 c. a handle at the opposite end of the member from said distal end for grasping by either hand, whereby said device, in response to movement thereof over the tongue, loosens, collects, and removes debris from the top surface of the tongue.

12. The device of claim 11 wherein, said textured surface is sandpaper-like in construction.

13. The device of claim 11 wherein, said textured surface is sawtooth-like in construction.

14. The device of claim 11 further including, a scraper extending along said perimeter of said distal end of said member.

15. The device of claim 14, further including, a transverse trough extending adjacent to said scraper.

* * * * *